US012607632B2

(12) United States Patent
Sutarlie et al.

(10) Patent No.: US 12,607,632 B2
(45) Date of Patent: Apr. 21, 2026

(54) NANOPARTICLE SOLUTIONS, KITS, DEVICES AND METHODS OF USE THEREOF

(71) Applicant: Agency for Science, Technology and Research, Singapore (SG)

(72) Inventors: Laura Sutarlie, Singapore (SG); Xiaodi Su, Singapore (SG); Yang Xu, Singapore (SG); Heng Li Chee, Singapore (SG); Sian Yang Ow, Singapore (SG); Takuya Sato, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 722 days.

(21) Appl. No.: 17/798,951

(22) PCT Filed: Feb. 11, 2021

(86) PCT No.: PCT/SG2021/050072
§ 371 (c)(1),
(2) Date: Aug. 11, 2022

(87) PCT Pub. No.: WO2021/162639
PCT Pub. Date: Aug. 19, 2021

(65) Prior Publication Data
US 2023/0075135 A1 Mar. 9, 2023

(30) Foreign Application Priority Data
Feb. 13, 2020 (SG) .......................... 10202001326W

(51) Int. Cl.
*G01N 33/569* (2006.01)
*G01N 33/543* (2006.01)
*G01N 33/58* (2006.01)

(52) U.S. Cl.
CPC . *G01N 33/56911* (2013.01); *G01N 33/54306* (2013.01); *G01N 33/588* (2013.01)

(58) Field of Classification Search
CPC ....... G01N 33/56911; G01N 33/54306; G01N 33/588
See application file for complete search history.

(56) References Cited

U.S. PATENT DOCUMENTS

2006/0079000 A1 4/2006 Floriano et al.

OTHER PUBLICATIONS

Sutarlie et al., "Nanomaterials-based biosensors for detection of microorganisms and microbial toxins" in Biotechnology Journal, 2016, 1-25. (Year: 2016).*

(Continued)

*Primary Examiner* — Blessing M Fubara
(74) *Attorney, Agent, or Firm* — Foley Hoag LLP; Lucas P. Watkins; Allison L. Gilder

(57) ABSTRACT

The present invention relates, in general terms, to nanoparticle solutions, kits, devices and methods of use thereof. The present invention is suitable for use in quantifying bacterial cells in a sample. The method of quantifying bacterial cells in a sample comprises passing the sample in a liquid form and an aqueous nanoparticle solution through a porous substrate such that the bacterial cells in the sample is trapped (Continued)

on the porous substrate and can be quantified by a colorimetric and/or fluorescence output emitted from the nanoparticle bound to the bacterial cells.

20 Claims, 10 Drawing Sheets

(56)                    References Cited

OTHER PUBLICATIONS

Su et al., "Colorimetric detection of *Escherichia coli* 0157:H7 using functionalized Au@Pt nanoparticles as peroxidase mimetic" in Analyst, 138:3026:3031 (2013). (Year: 2013).*

Jin et al., "Upconversion nanoparticles based FRET aptasensor for rapid and ultrasensitive bacteria detection" in Biosensors and Bioelectronics, (90): 525-533 (2017). (Year: 2017).*

Catala et al., "Online SERS Quantification of *Staphylococcus aureus* and the Application to Diagnostics in Human Fluids" in Advanced Material Technologies, 160163: 1-9 (2016). (Year: 2016).*

Liopo et al., "Controlled Bacteria-Gold Nanorod Interactions for Enhancement of Optoacoustic contract", in Progress in Biomedical Optics and Imaging, 8943: 1-10 (2015). (Year: 2015).*

Sutarlie et al., "Nanomaterials-based biosensors for detection of microorganisms and microbial toxins" in Biotechnology Journal, 2017, 12, 1500459 (1-25). (Year: 2017).*

Catala et al., "Online SERS Quantification of *Staphylococcus aureus* and the Application to Diagnostics in Human Fluids" Advanced Material Technologies, 160163: 1-9 (2016).

Gao et al., " Screening Lectin-Binding Specificity of Bacterium by Lectin Microarray with Gold Nanoparticle Probes" Analytical Chemistry, 82(22): 9240-9247 (2010).

International Search Report and Written Opinion for International Application No. PCT/SG2021/050072 dated Apr. 22, 2021.

Jin et al., " Upconversion nanoparticles based FRET aptasensor for rapid and ultrasenstive bacteria detection" Biosensors and Bioelectronics, (90): 525-533 (2017).

Liopo et al., "Controlled Bacteria—Gold Nanorod Interactions for Enhancement of Optoacoustic Contrast" Progress in Biomedical Optics and Imaging, 8943: 1-10 (2015).

Liu et al., "Detection of Pathogens Using Luminescent CdSe/ZnS Dendron Nanocrystals and a Porous Membrane Immunofilter" Analytical Chemistry, 79: 8796-8802 (2007).

Ravikumar et al., "Surface modified glass substrate for sensing *E. coli* using highly stable and luminescent CdSe/CdS core shell quantum dots" Journal of Photochemistry and Photobiology, 204: Article 111799 (2020).

Su et al., "Colorimetric detection of *Escherichia coli* O157:H7 using functionalized Au@Pt nanoparticles as peroxidase mimetics" Analyst, 138: 3026-3031 (2013).

Sutarlie et al., "Nanomaterials-based biosensors for detection of microorganisms and microbial toxins" Biotechnology Journal, 11: 1-25 (2016).

* cited by examiner (b)

NANOPARTICLE SOLUTIONS, KITS, DEVICES AND METHODS OF USE THEREOF

RELATED APPLICATIONS

This application is a § 371 national-stage application based on PCT/SG2021/050072, filed Feb. 11, 2021 which claims the benefit to Republic of Singapore Patent Application Number 10202001326W, filed Feb. 13, 2020, each of which is hereby incorporated by reference in its entirety.

TECHNICAL FIELD

The present invention relates, in general terms, to nanoparticle solutions, kits, devices and methods of use thereof. The present invention is suitable for use in quantifying bacterial cells in a sample.

BACKGROUND

Conventional methods used to detect and quantify bacteria are plate culturing, polymerase chain reaction (PCR), enzyme linked immunosorbent assay (ELISA) and chemical sensors based detection. However, such methods do not provide a quick readout of total bacteria count and requires a skilled person to work the method.

For example, the current industrial standard for bacteria detection is based on bacteria plate counting (plate culturing). This method takes about 2 to 7 days to obtain results, as the bacterial cells need to grow and multiply. Further, sample transfer to a laboratory is required, and the method cannot detect unculturable bacteria.

Accordingly, there is a need of a rapid on-site bacteria test for total bacteria count. There is a further need for such a test in the food and beverage (F&B) industry and many other industries, e.g. water industry, agriculture, aqua-culture, medical and pharmaceutical industries. There is also a need to have a reliable quantification method, which is easy to handle for use on site of the above mentioned industries.

It would be desirable to overcome or ameliorate at least one of the above-described problems, or at least to provide a useful alternative.

SUMMARY

The present invention is predicated on the understanding that there is a lack of a simple yet rapid bacteria quantification test. Most current bacteria quantification tests require some sample treatment such as bacteria enrichment, or uses enzymatic reaction which can be easily affected by pH and temperature, or gives a delayed response. Accordingly, these bacteria quantification devices can be inaccurate as it is dependent on the sample preparation. For example, when nanoparticles are used to target bacterial cells, a source of error can come from the tendency of nanoparticles to self-aggregate, thus giving a false indication that bacterial cells are present. Another source of inaccuracy can be in the binding of nanoparticles to particulates other than bacterial cells. In addition, the quantification of live bacterial cells in contrast to dead bacterial cells should be distinguished as the presence of live bacterial cells is the cause of hygiene and health concerns while dead bacterial cells, if present after a sterilisation process, is generally not a health concern. The inventors have found that certain features as disclosed herein are beneficial for providing a bacterial cell quantification device which is rapid and at the same time accurate.

The present invention discloses a method of quantifying bacterial cells in a sample, comprising:

a) passing the sample in a liquid form through a porous substrate, the porous substrate for trapping or retaining bacterial cells on its surface thereof;

b) passing an aqueous nanoparticle solution through the porous substrate, the aqueous nanoparticle solution comprising a plasmonic and/or fluorescent nanoparticle and a first ionic surfactant, the nanoparticle functionalised with an affinity probe for binding to said bacterial cells trapped or retained on the surface of the substrate via affinity binding; and c) passing a second aqueous solution through the porous substrate, the second aqueous solution for washing the unbound nanoparticle from the porous substrate;

wherein the bacterial cells in the sample is quantifiable by a colorimetric and/or fluorescence output emitted from the nanoparticle bound to the bacterial cells.

In some embodiments, the first ionic surfactant is selected from cetrimonium bromide (CTAB), cetrimonium chloride (CTAC) or sodium dodecyl sulfate (SDS).

Advantageously, the ionic surfactant provides a charged environment such that the nanoparticles are stabilised within the nanoparticle solution. This eliminates (or at least reduces) self-aggregation of the nanoparticles. It also reduces or eliminates non-specific binding to particulates which are not bacterial cells. The ionic surfactant also prevents non-specific background staining on the porous substrate.

In some embodiments, the first ionic surfactant in the first solution is at a concentration of at least 2 mg/mL.

In some embodiments, the plasmonic and/or fluorescent nanoparticle is selected from metallic nanoparticles, II-VI binary, ternary and quaternary semiconductor nanocrystals, IV-VI semiconductor nanocrystals, III-V semiconductor nanocrystals, I-V semiconductor nanocrystals, I-III-V semiconductor nanocrystals, group IV elemental semiconductor nanocrystals, $Cu^+$ and $Mn^{2+}$ doped semiconductor nanocrystals, and their related core/shell structures thereof.

In some embodiments, the plasmonic and/or fluorescent nanoparticle is selected from gold nanoparticles, silver nanoparticles or CdSe/CdS core/shell nanorods.

In some embodiments, the nanoparticle is functionalised with an affinity probe selected from protein, sugar binding protein, peptide, or aptamer, such as *Griphonia simplicifolia* II (GSII) lectin, BSA, and Antibac2 (AB2) aptamer. This is based on the affinity probe's specific recognition of commonalities in bacteria cells.

Advantageously, the presence of an affinity probe allows for rapid targeting of bacterial cells by the nanoparticle due to the low activation barrier. Further, affinity probe allows for a distinction between live and dead bacterial cells as the affinity interaction is reversible.

In some embodiments, a ratio of affinity probe to nanoparticle is about 1:1 to about 100:1.

In some embodiments, the nanoparticle is at a concentration of about 2 nM to about 30 nM.

In some embodiments, step (b) further comprises incubating the porous substrate with the first solution for at least 10 min.

In some embodiments, the nanoparticle is attachable to the bacterial cells via non-covalent interaction.

In some embodiments, the nanoparticle is attachable to the bacterial cells via electrostatic interaction, ionic bonding, Hydrogen bonding, Van der Waals interaction or a combination thereof.

In some embodiments, the second aqueous solution is a protein dissociation buffer such as glycine-HCl buffer at about pH 2.8 to about pH 3.5, or citric acid buffer at about pH 3.

In some embodiments, the second aqueous solution comprises a second surfactant selected from Tween-20, CTAB, CTAC, SDS.

Advantageously, the second solution when used to wash the bacterial cell sample allows for the preferential quantification of live bacterial cells over dead bacterial cells by disturbing the affinity interaction of the nanoparticle with dead bacterial cells, which is not as strong as with live bacterial cells.

In some embodiments, the second surfactant in the second aqueous solution is at a concentration of about 0.5 wt/wt % to about 1 wt/wt %.

In some embodiments, step (c) further comprises incubating the porous substrate with the second aqueous solution for at least 10 min.

In some embodiments, the colorimetric and/or fluorescence output emitted from the nanoparticle bound to the bacterial cells is measured or quantified by detecting a colorimetric and/or fluorescence output from the nanoparticles on the porous substrate.

In some embodiments, the colorimetric and/or fluorescence output emitted from the nanoparticle bound to the bacterial cells is detectable by eye.

In some embodiments, the method further comprises a step of quantifying the colorimetric and/or fluorescence output emitted from the nanoparticle bound to the bacterial cells via a detector.

In some embodiments, the method is for quantifying Gram-positive and/or Gram-negative bacterial cells in the sample.

In some embodiments, live bacterial cells in a sample is quantifiable from about $10^2$ cfu/mL to about $10^9$ cfu/mL.

In some embodiments, dead bacterial cells in a sample is quantifiable from more than about $10^7$ cfu/mL.

The present invention also discloses a device for quantifying bacterial cells in a sample in a liquid form, comprising:
   a) a porous substrate for trapping or retaining the bacterial cells on its surface thereof; and
   b) an aqueous nanoparticle solution comprising a plasmonic and/or fluorescent nanoparticle and a first ionic surfactant, the nanoparticle functionalised with an affinity probe for binding to said bacterial cells trapped or retained on the surface of the substrate via affinity binding; and
   c) a second aqueous solution for washing the unbound nanoparticle from the porous substrate;
wherein the bacterial cells in the sample is quantifiable by a colorimetric and/or fluorescence output emitted from the nanoparticle bound to the bacterial cells.

In some embodiments, the porous substrate has a pore size of about 0.22 μm.

Advantageously, the porous substrate allows for the bacterial cells to be trapped on its surface while allowing other particulates to pass through. This provides for a high accuracy. Further, the aqueous solutions are allowed to flow through unhindered, thus shortening the time for quantification.

In some embodiments, the device further comprises a detector for quantifying the colorimetric and/or fluorescence output emitted from the nanoparticle bound to the bacterial cells.

In some embodiments, the device is for quantifying Gram-positive and/or Gram-negative bacterial cells in the sample.

In some embodiments, the limit of detection for live bacterial cells in a sample is about $10^2$ cfu/mL.

In some embodiments, the limit of detection for dead bacterial cells in a sample is about $10^7$ cfu/mL.

The present invention discloses an aqueous nanoparticle solution, comprising:
   a) a plasmonic and/or fluorescent nanoparticle; and
   b) a first ionic surfactant;
wherein the nanoparticle is functionalised with an affinity probe.

The present invention also discloses a kit, comprising:
   a) an aqueous nanoparticle solution, the aqueous nanoparticle solution comprising:
      i) a plasmonic and/or fluorescent nanoparticle; and
      ii) a first ionic surfactant;
wherein the nanoparticle is functionalised with an affinity probe; and
   b) a second aqueous solution.

BRIEF DESCRIPTION OF THE DRAWINGS

Embodiments of the present invention will now be described, by way of non-limiting example, with reference to the drawings in which.

DETAILED DESCRIPTION

The technical challenges in relation to the present invention includes an understanding of the affinity probes' biochemical properties, charges, functional groups, as well as the membrane's surface properties, in order to derive a suitable formulation to prevent the non-specific background staining, and at the same time retain the affinity interaction between the particles and the bacteria cells. In addition to the proper selection of suitable surfactants, optimizing the surfactant concentration can also be important to minimize the non-specific staining without introducing crystallization of surfactant (due to too high concentration of surfactant).

Accordingly, the present invention discloses a method of quantifying bacterial cells in a sample, comprising:

a) flowing the sample through a porous substrate, the porous substrate for trapping or retaining bacterial cells on its surface thereof;

b) flowing an aqueous nanoparticle solution through the porous substrate, the aqueous nanoparticle solution comprising a plasmonic and/or fluorescent nanoparticle and a first ionic surfactant, the nanoparticle functionalised with an affinity probe for binding to said bacterial cells trapped or retained on the surface of the substrate via affinity binding; and c) flowing a second aqueous solution through the porous substrate, the second aqueous solution for washing the unbound nanoparticle from the porous substrate;

wherein the bacterial cells in the sample is quantifiable by a colorimetric and/or fluorescence output emitted from the nanoparticle bound to the bacterial cells.

Figure 1:
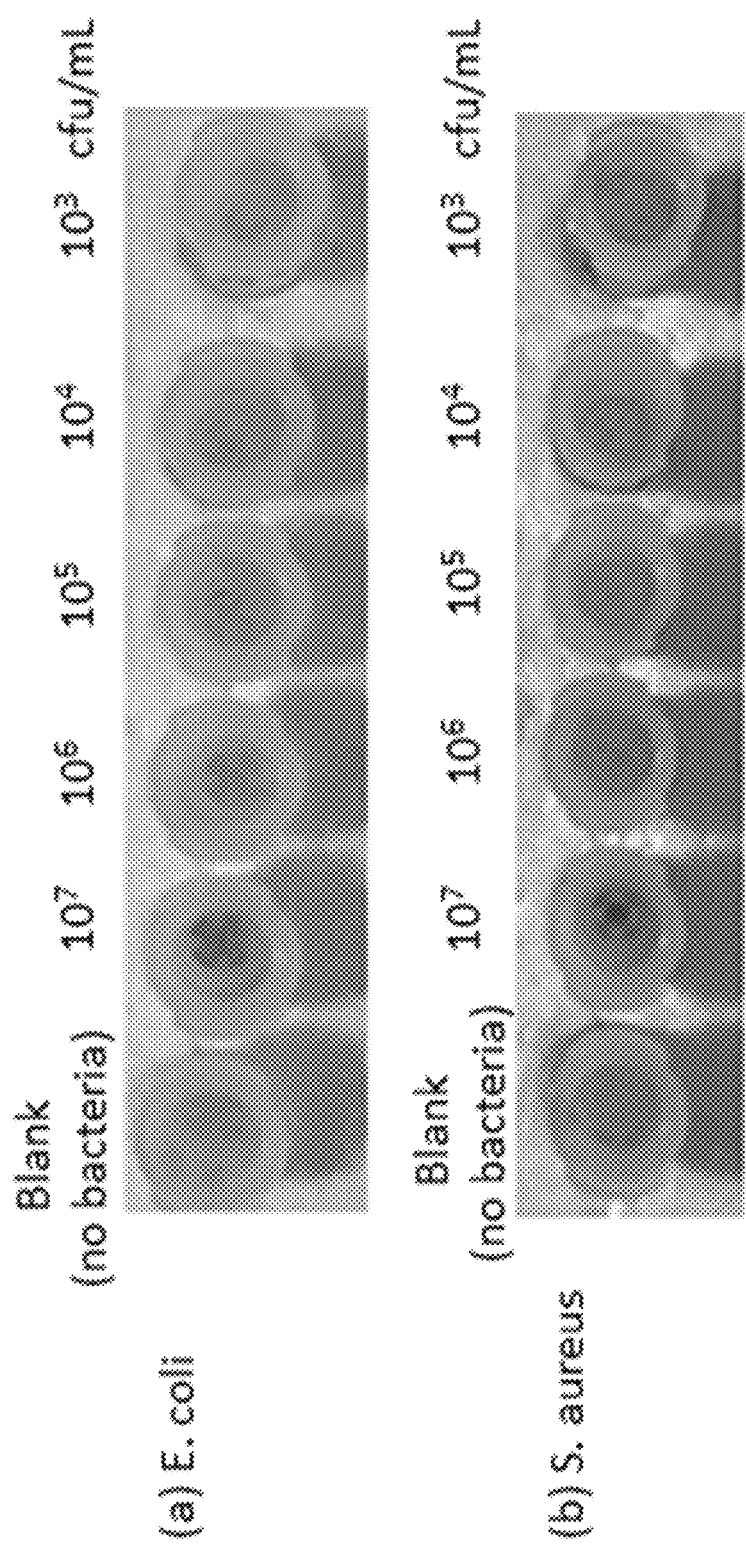
FIG. 1 illustrates visual outcome of GSII-AuNPs staining in "filter & stain" method for (a) E. coli and (b) S. aureus in water ($10^3$-$10^7$ cfu/mL); images were taken by using a mobile phone camera.
Figure 3:
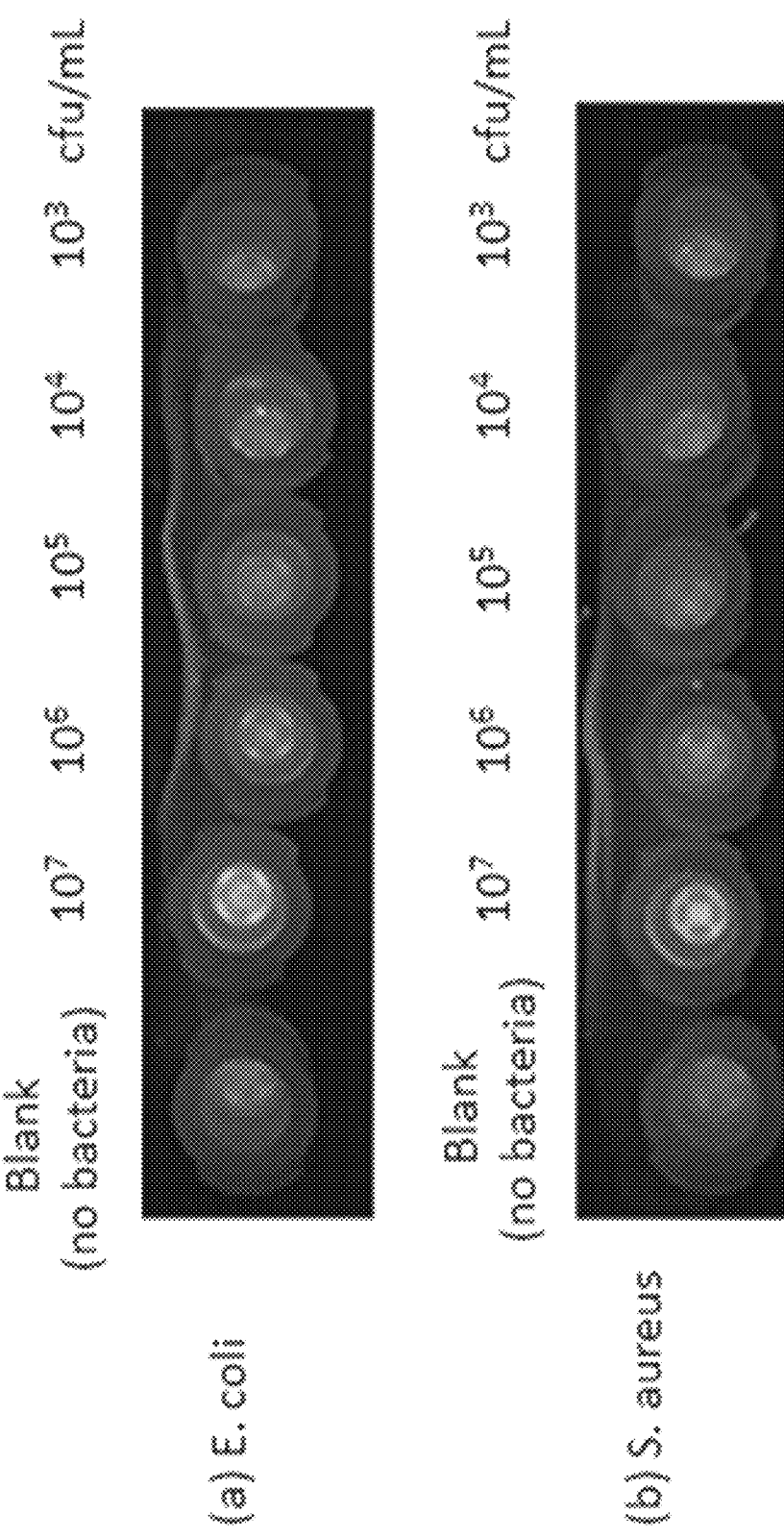
FIG. 3 illustrates visual outcome of GSII-QNRs staining in "filter & stain" method for (a) E. coli and (b) S. aureus in water ($10^3$-$10^7$ cfu/mL); images were taken by using a mobile phone camera under UV light (365 nm) for excitation.
Figure 4:
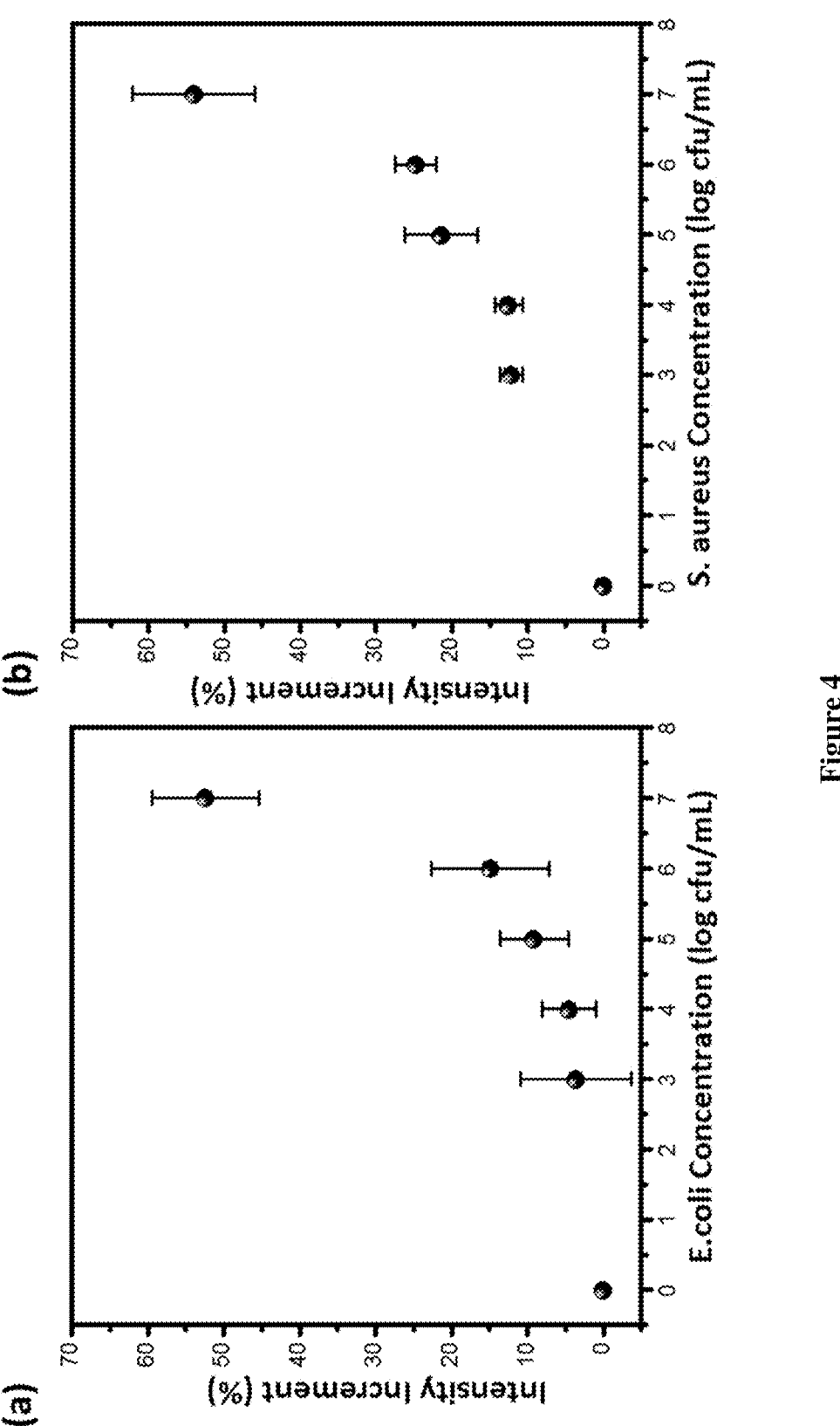
FIG. 4 illustrates percentage of intensity increment obtained from GSII-QNRs stain for (a) E. coli and (b) S. aureus in water as measured by image analysis.
Figure 6:
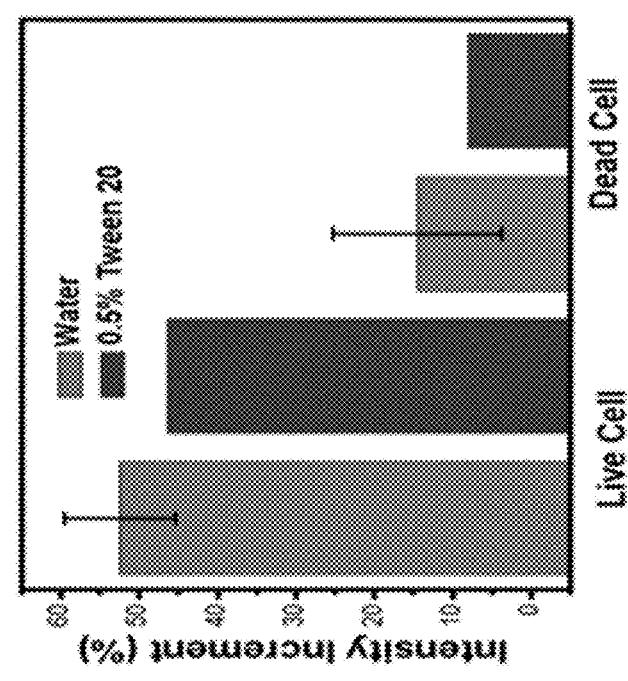
FIG. 6 illustrates (a) visual outcome of GSII-QNRs staining in "filter & stain" method for live and dead E. coli cells at $10^7$ cfu/mL by using Tween-20 (0.5% in water) for washing, (b) Comparison of intensity increment (%) for $10^7$ cfu/mL live cells and dead cells in "filter & stain" assay by using water (pink bar) and 0.5% Tween-20 (blue bar) in the washing step.

In some embodiments, the method is for quantifying live bacterial cells in a sample. Accordingly, the method is able to distinguish between live bacterial cells and dead bacterial cells. For example, as shown in FIGS. 1 and 3, the method can detect both Gram-positive (e.g. *S. aureus*) and Gram-negative (e.g. *E. coli*) bacteria. Further, as shown in FIG. 6, the method preferentially detects live cells. Dead cells at a high concentration of $10^7$ CFU/ml do not show detection signal.

As used herein, 'bacterial cell quantification' refers to the measurement or determination of the total number of bacterial cells in a sample. In this regard, there is no distinction regarding the species/type of bacterial cells. In some embodiments, the total number of bacterial cells is the total number of live bacterial cells. The sample can be an unadulterated sample or unprocessed sample. The sample can be a processed sample, for example a diluted sample or a concentrated/neat sample.

As used herein, "flowing" refers to moving the sample continuously as a stream through the porous substrate. In some embodiments, the sample (and/or the solutions) is passed through the porous substrate. The sample contacts the porous substrate at one surface, permeates the porous substrate and exits the porous substrate via an opposite surface. To this end, the sample is in a liquid form.

In some embodiments, the method of quantifying bacterial cells in a sample comprises:

a) passing the sample in a liquid form through a porous substrate, the porous substrate for trapping or retaining bacterial cells on its surface thereof;

b) passing an aqueous nanoparticle solution through the porous substrate, the aqueous nanoparticle solution comprising a plasmonic and/or fluorescent nanoparticle and a first ionic surfactant, the nanoparticle functionalised with an affinity probe for binding to said bacterial cells trapped or retained on the surface of the substrate via affinity binding; and c) passing a second aqueous solution through the porous substrate, the second aqueous solution for washing the unbound nanoparticle from the porous substrate;

wherein the bacterial cells in the sample is quantifiable by a colorimetric and/or fluorescence output emitted from the nanoparticle bound to the bacterial cells.

The passing of the sample in a liquid form through a porous substrate serves to trap or retain bacterial cells on the surface of the substrate. In some embodiments, the sample is filtered through the porous substrate. This step allows for the separation of bacterial cells from the other contents in the sample which can result in a high background noise.

As used herein, 'aqueous solution' refers to a water based solvent or solvent system, and which comprises of mainly water. Such solvents can be either polar or non-polar, and/or either protic or aprotic. Solvent systems refer to combinations of solvents which resulting in a final single phase. Both 'solvents' and 'solvent systems' can include, and is not limited to, pentane, cyclopentane, hexane, cyclohexane, benzene, toluene, dioxane, chloroform, diethylether, dichloromethane, tetrahydrofuran, ethyl acetate, acetone, dimethylformamide, acetonitrile, dimethyl sulfoxide, nitromethane, propylene carbonate, formic acid, butanol, isopropanol, propanol, ethanol, methanol, acetic acid, ethylene glycol, diethylene glycol or water. Water based solvent or solvent systems can also include dissolved ions, salts and molecules such as amino acids, proteins, sugars and phospholipids. Such salts may be, but not limited to, sodium chloride, potassium chloride, ammonium acetate, magnesium acetate, magnesium chloride, magnesium sulfate, potassium acetate, potassium chloride, sodium acetate, sodium citrate, zinc chloride, HEPES sodium, calcium chloride, ferric nitrate, sodium bicarbonate, potassium phosphate and sodium phosphate. As such, biological fluids, physiological solutions and culture medium also fall within this definition. In most embodiments, the aqueous solution is water. In some embodiments, the aqueous solution is deionised water. In some embodiments, the aqueous solution is Millipore water.

An aqueous solution is advantageously used in the present disclosure. In particular, water is used. Water is a green solvent and can be manipulated by the user with ease, without concern of toxicity and change in concentration due to evaporation. Water also does not adversely impact the porous substrate.

'Nanoparticle' refers to a nano-object with all three external dimensions in the nanoscale. For example, nanoparticle can be particles between 1 nm and 990 nm in size. In an embodiment, the nanoparticle is less than about 100 nm in diameter. Because of their nano-size, properties which are different from the physical bulk properties are manifested.

'Plasmonic nanoparticle' refer to particles whose electron density can couple with electromagnetic radiation of wavelengths that are far larger than the particle due to the nature of the dielectric-metal interface between the medium and the particles. What differentiates these particles from normal surface plasmons is that plasmonic nanoparticles also exhibit interesting scattering, absorbance, and coupling properties based on their geometries and relative positions. Plasmons are the oscillations of free electrons that are the consequence of the formation of a dipole in the material due to electromagnetic waves. The electrons migrate in the material to restore its initial state; however, the light waves oscillate, leading to a constant shift in the dipole that forces the electrons to oscillate at the same frequency as the light. This coupling only occurs when the frequency of the light is equal to or less than the plasma frequency and is greatest at the plasma frequency that is therefore called the resonant frequency. The scattering and absorbance cross-sections describe the intensity of a given frequency to be scattered or absorbed. Examples of plasmonic nanoparticle are, but not limited to, gold nanoparticles and silver nanoparticles.

'Fluorescent nanoparticle' refer to particles which are able to emit light (fluoresce) after excitation with electromagnetic radiation of a certain wavelength. In most cases, the emitted light has a longer wavelength, and therefore lower energy, than the absorbed radiation. Fluorescent nanoparticle ceases to glow nearly immediately when the radiation source stops.

In some embodiments, the plasmonic and/or fluorescent nanoparticle is selected from metallic nanoparticles, IT-VI binary, ternary and quaternary semiconductor nanocrystals, IV-VI semiconductor nanocrystals, III-V semiconductor nanocrystals, I-V semiconductor nanocrystals, I-III-V semiconductor nanocrystals, group IV elemental semiconductor nanocrystals, $Cu^+$ and $Mn^{2+}$ doped semiconductor nanocrystals, and their related core/shell structures thereof. In some embodiments, the plasmonic and/or fluorescent nanoparticle is selected from gold nanoparticles, silver nanoparticles or CdSe/CdS core/shell nanorods. In other embodiments, the plasmonic and/or fluorescent nanoparticle is a semiconductor nanoparticle. In other embodiments, the plasmonic and/or fluorescent nanoparticle is a semiconductor nanorod. An example of a semiconductor nanorod is CdSe/CdS core/shell nanorods. Examples of II-VI binary, ternary and quaternary semiconductor nanocrystals and related core/shell structures are CdSe, CdZnS, CdZnSeS, CdSe/ZnS; examples of IV-VI semiconductor nanocrystals and related core/shell structures are PbSe, PbSe/PbS; examples of III-V semiconductor nanocrystals and related core/shell structures are InP, InAs, InP/ZnS; example of I-V semiconductor nanocrystals and related core/shell structures is $Ag_2S$; examples of I-III-V semiconductor nanocrystals and related core/shell structures are $AgInS_2$, $CuInS_2/ZnS$; examples of elemental group IV semiconductor nanocrystals are Carbon dots and Si nanocrystals; examples of $Cu^+$ and $Mn^{2+}$ doped semiconductor nanocrystals are $Cu^+$ doped ZnSe/ZnS, and $Mn2^+$ doped ZnS. Other examples of such nanocrystals are CdSe/ZnS, CdTe, CdZnS/ZnS, CdZnSeS, $CuInS_2/ZnS$, $CuInSe_2/ZnS$, CuInZnS/ZnS, PbS, PbSe/PbS, InP/ZnS, $Ag_2S$, $Ag_2Se$ and $AgInS_2/ZnS$. Another example of a plasmonic nanoparticle is platinum nanoparticle.

The skilled person would understand that, for example, Group 14 (IUPAC notation) is the same as Group IV. For avoidance of doubt, group 14 (or group IV) includes elements such as carbon, silicon, germanium, tin and lead. As another example, II-VI semiconductor compounds are compounds composed of a metal from either group 2 or 12 of the periodic table (the alkaline earth metals and group 12 elements, formerly called groups IIA and IIB) and a non-metal from group 16 (the chalcogens, formerly called group VI).

In some embodiments, the nanoparticles have a high plasmonic or fluorescence output. For example, semiconductor nanorods can be used instead of semiconductor nanodots. The inventors have found that a fluorescence intensity in excess of 10 times that of nanodots can be obtained if nanorods are used. Without wanting to be bound by theory, it is believed that semiconductor nanorods that are brighter than their spherical quantum dots counterpart due to larger action cross section (defined as light absorption cross-section multiplied by quantum yield) than spherical quantum dots under the same excitation and emission wavelength. This is advantageous as it allows for ease of detection, especially if by eye. As another example, gold nanorods can be used instead of gold nanospheres to increase the colorimetric intensity.

In some embodiments, the nanoparticle is at a concentration of about 2 nM to about 30 nM. In other embodiments, when the nanoparticle is a gold nanoparticle, the nanoparticle is at a concentration of about 5 nM to about 30 nM, or about 8 nM to about 20 nM. In other embodiments, when the nanoparticle is a semiconductor nanorod, the nanoparticle is at a concentration of about 2 nM to about 15 nM, or about 3 nM to about 10 nM.

The affinity probe allows for affinity binding to bacterial cells. As used herein, 'affinity interaction' refers to the interaction between biological molecules and/or organisms which can be characterized by a binding affinity. High-affinity binding results from greater intermolecular force between the biological entities while low-affinity ligand binding involves less intermolecular force between them. Such intermolecular forces can for example be hydrogen bonding, electrostatic interaction, hydrophobic and/or Van der Waals forces. Accordingly, as used herein, 'affinity probe' or affinity-based probe' refers to chemical probes that interact with bacterial cells based on these intermolecular force. Covalent interaction is hence excluded from this scope. Such affinity probes can be selected based on their specific recognition of commonalities in general bacteria cells. For example, affinity probes for binding to bacterial cell moieties are: GSII to peptidoglycans, BSA to peptidoglycan and bacterial lipid, and AB2 aptamer to peptidoglycans. These interactions were tested and their affinity to various bacteria cells confirmed through binding characterisation tests.

The use of affinity probe can be advantageous due to its relative speed and specificity. This is in contrast to, for example, using glutaraldehyde as a crosslinking agent for binding nanoparticles to bacterial cells. While glutaraldehyde can crosslink between amine functional group on the nanoparticles and amine groups on bacteria cells through aldehyde and amine reaction to form imine, glutaraldehyde is not specific to bacterial cells and can also react with other amine groups, such as amines in proteins, polymers, amino acids that are not from bacteria cells. Accordingly, assays based on glutaraldehyde can result in a high sample background. Further, glutaraldehyde-based crosslinking is a covalent interaction and requires at least about 80 min to crosslink the amine functionalized nanoparticles with bacteria cells.

Accordingly, in some embodiments, the nanoparticle is functionalised with an affinity probe selected from protein, sugar binding protein, peptide or aptamer. These affinity probes can recognize the commonalities on bacterial cells, e.g. peptidoglycans or common bacterial proteins/lipids on the cell wall of Gram Negative and Gram Positive bacteria. For example, the affinity probe can be selected from *Griphonia simplicifolia* II (GSII) lectin, BSA, and Antibac2 (AB2) aptamer.

Advantageously, the presence of an affinity probe allows for rapid targeting of bacterial cells by the nanoparticle due to the low activation barrier. Further, affinity probe allows for the distinction between live and dead bacterial cells as the affinity interaction is reversible. Further advantageously, it was found that while nanoparticles are small enough to be internalized by bacterial cells, when nanoparticles are functionalised with affinity based probes, the nanoparticles are preferentially localized on the surface as they prefer to bind to the molecules on the surface of the live bacterial cells (through affinity binding). Dead bacterial cells with compromised cell membrane can internalize nanoparticles which can also be easily removed via the washing step. This provides for the high accuracy with a low false positive. In short, internalization of the nanoparticles is going to be of a much lower magnitude as adsorption to the target on the surface.

In some embodiments, the affinity probe is provided at a concentration of about 0.01 mg/mL to about 1 mg/mL. In other embodiments, the concentration is about 0.1 mg/mL to about 1 mg/mL, about 0.1 mg/mL to about 0.9 mg/mL, about 0.1 mg/mL to about 0.8 mg/mL, about 0.1 mg/mL to about 0.7 mg/mL, about 0.1 mg/mL to about 0.6 mg/mL, about 0.1 mg/mL to about 0.5 mg/mL, about 0.1 mg/mL to about 0.4 mg/mL, or about 0.1 mg/mL to about 0.3 mg/mL.

The amount of the affinity probe on the nanoparticles is about 1-100 molecules per particle. This is dependent on the size of the particle, size of the affinity probe, and conjugation method. In some embodiments, the ratio of affinity probe to nanoparticle is about 1:1 to about 100:1. In other embodiments, the ratio is about 5:1 to about 100:1, about 10:1 to about 100:1, about 20:1 to about 100:1, about 30:1 to about 100:1, about 40:1 to about 100:1, about 50:1 to about 100:1, about 50:1 to about 90:1, or about 50:1 to about 80:1.

Further, this is advantageous in that the nanoparticles can be used to target commonalities on bacteria cells, and are thus specific to bacterial cells detection and can be used for detection in complex sample matrix. This is in contrast to crosslinking agent which utilises covalent bond formation to adhere particles to specific bacterial cells.

As used herein, 'surfactant' is a compound that lower the surface tension (or interfacial tension) between two liquids, between a gas and a liquid, or between a liquid and a solid. For example, the surfactant can reduce the surface tension between a liquid and a nanoparticle. Surfactants contain both hydrophobic groups (their tails) and hydrophilic groups (their heads). Therefore, a surfactant contains both a water-insoluble (or oil-soluble) component and a water-soluble component. Surfactants will diffuse in water and adsorb at interfaces between water and the nanoparticle. The water-insoluble hydrophobic group may be in contact with the nanoparticle surface, while the water-soluble head group remains in the water phase. Alternatively, the surfactant may form a bilayer around the nanoparticle surface, with the hydrophobic layer being protected by hydrophilic heads at both sides, with one side adjacent to the nanoparticle surface and the other adjacent to the water phase.

In some embodiments, the first ionic surfactant is a cationic surfactant, an anionic surfactant or a zwitterionic surfactant. In other embodiments, the first ionic surfactant is selected from cetrimonium bromide (CTAB), cetrimonium chloride (CTAC) or sodium dodecyl sulfate (SDS). Advantageously, the ionic surfactant prevents, or at least reduces, the aggregation of the nanoparticles by providing a charged environment such that the nanoparticles are stabilised within the nanoparticle solution. It also acts to stabilise the affinity probes and improves the shelf-life of the solution. The ionic surfactant also acts to reduce non-specific binding to particulates which are not bacterial cells. The ionic surfactant also prevents non-specific background staining on the porous substrate. In this regard, the inventors have found that the ionic surfactant allows for the passivation of the porous substrate, which acts as a barrier to prevent the aggregation of the nanoparticles on the porous substrate. In contrast, non-ionic surfactants such as Tween 20 was found to increase non-specific binding of nanoparticles on the porous substrate.

In some embodiments, the first ionic surfactant in the first solution is at a concentration of at least 2 mg/mL. In other embodiments, the concentration is at least 3 mg/mL, 4 mg/mL, 5 mg/mL, 6 mg/mL, 8 mg/mL, 10 mg/mL, 15 mg/mL or 20 mg/mL. In other embodiments, when the first ionic surfactant is CTAB, the concentration is about 4 mg/mL to about 6 mg/mL. The inventors have found that for CTAB, at concentration lower than 4 mg/mL, the nanoparticles will still have non-specific binding on filter membrane while at concentration higher than 6 mg/ml, CTAB will crystallize at room temperature upon storage.

Advantageously, the inventors have found the nanoparticle solution is stable in that the nanoparticles do not aggregate or phase separate over time. This allows for a good shelf-life. Further, the ionic surfactant eliminates or at least reduces non-specific binding to particulates other than bacterial cells. In addition, non-specific binding to the porous substrate is also eliminated or at least reduced.

Step (b) can further comprise a step of incubating the porous substrate with the first solution for at least 5 min. In other embodiments, the incubation is for at least 10 min, 15 min, 20 min or 30 min. In other embodiments, the incubation is about 5 min to about 35 min, or about 10 min to about 30 min. This incubation step can be advantageous in improving the interaction of the nanoparticles with the bacterial cells. This time can be selected such that the localisation of the nanoparticles on the surface of the bacterial cells reaches equilibrium.

In some embodiments, due to the presence of affinity probes on the surface of the nanoparticles, the nanoparticle is attachable to the bacterial cells via intermolecular interaction. In some embodiments, the nanoparticle is attachable to the bacterial cells via non-covalent interaction. For example, the nanoparticle can be attachable to the bacterial cells via electrostatic interaction, ionic bonding, Hydrogen bonding, Van der Waals interaction or a combination thereof. The nanoparticle can also be attachable to the bacterial cells via hydrophobic and/or hydrophilic pockets on the bacterial cells through like-like interaction.

The second aqueous solution can be a protein dissociation buffer. Such buffers are advantageously suitable as they do not adversely alter the protein structure when dispersed in solution. For example, glycine-HCl buffer at about pH 2.8 to about pH 3.5 or citric acid buffer at about pH 3 can be used. Alternatively, the second aqueous solution can comprise a second surfactant. The second surfactant can be an ionic surfactant, such as cationic surfactant, anionic surfactant or Zwitterionic surfactant. Such surfactants can be, for example, selected from Tween-20, CTAB, CTAC, SDS.

Advantageously, the second solution when used to wash the bacterial cell sample allows for the preferential quantification of live bacterial cells over dead bacterial cells by disturbing the affinity interaction of the nanoparticle with dead bacterial cells, which is not as strong as with live bacterial cells.

In some embodiments, the second surfactant in the second aqueous solution is at a concentration of about 0.5 wt/wt % to about 1 wt/wt %. In other embodiments, the concentration is about 0.5 wt/wt % to about 0.9 wt/wt %, 0.6 wt/wt % to about 0.9 wt/wt %, about 0.5 wt/wt % to about 0.8 wt/wt %, or 0.6 wt/wt % to about 0.8 wt/wt %. In this regard, if the surfactant concentration is too high, the nanoparticles bound to live bacterial cells also can be significantly removed without leaving much staining signal.

The inventors have found that at this particular concentration, nanoparticles can be washed off dead bacterial cells with minimal agitation/force such that an acceptable false positive can be obtained. If the concentration of the surfactant in the second solution is too low, most of the nanoparticles are not washed off, while if the concentration is too high, nanoparticles bound to live bacterial cells are also washed off. In this regard, the 'staining' on live bacterial cells is retained, and 'staining' on dead bacteria cells are effectively removed due to it being weakly bound.

Step (c) can further comprise a step of incubating the porous substrate with the second aqueous solution for at least 5 min. In other embodiments, the incubation is for at least 10 min, 15 min, 20 min or 30 min. In other embodiments, the incubation is about 5 min to about 35 min, or about 10 min to about 30 min.

In some embodiments, the porous substrate (filter) has a pore size of about 0.22 µm. In other embodiments, the pore size is less than 0.22 µm. In other embodiments, the pore size is more than 0.10 µm. In other embodiments, the pore size is about 0.1 µm to about 0.22 µm. In other embodiments, the porous substrate is a PVDF filter membrane, nylon or hydrophilic PTFE. In other embodiments, the porous substrate is a hydrophilic membrane.

Advantageously, the porous substrate allows for the bacterial cells to be trapped on its surface while allowing other particulates to pass through. This provides for a high accuracy and reduces the interference from other coloured and/or fluorescent particulates in the sample. In this regard, the coloured and/or fluorescent particulates passes through the porous substrate and are removed. Further, the aqueous solutions are allowed to flow through unhindered and without an excessive build-up of pressure, thus shortening the time for bacterial cells quantification.

It should be highlighted that the compatibility of the porous substrate (e.g. based on pore size) with the bacteria sample and nanoparticle solution can influence the quantification outcome.

In some embodiments, the method further comprises a step prior to (a) of flowing the sample through a pre-filter. In some embodiments, the pre-filter has a pore size of about 5 µm, or more than 5 µm. In other embodiments, the pre-filter comprises Nylon, (polyvinylidene difluoride) PVDF or other hydrophilic membrane that does not adsorb bacteria cells. The pre-filter is intended to remove larger particulates, if necessary. This may interfere with the quantification as larger particulates may block the filter which traps the bacteria cells. The inventors have further found that the pre-filter should not contain glass fibre as they may cause the adherence of bacteria cells to the pre-filter. The use of a pre-filter is an optional step, and can be considered when the skilled person encounters difficulties in passing the sample through the porous substrate, which indicates the presences of larger particulates.

In some embodiments, the colorimetric and/or fluorescence output emitted from the nanoparticle bound to the bacterial cells is detectable by eye. This can be based on the type of nanoparticle used. In some embodiments, when plasmonic nanoparticles are used, the limit of detection for the colorimetric output to be detectable by eye is about $10^2$ CFU/ml to about $10^6$ CFU/ml. In other embodiments, when fluorescence nanoparticles are used, the limit of detection for the fluorescence output to be detectable by eye is about $10^4$ CFU/ml. For example, when gold nanoparticles functionalised with GSII or BSA is used, the limit of detection for detection by eye is about $10^6$ CFU/ml. When gold nanoparticles functionalised with AB2 aptamer is used, the limit of detection for detection by eye is about $10^2$ CFU/ml. When semiconductor nanorods functionalised with GSII is used, the limit of detection for detection by eye is about $10^4$ CFU/ml.

The method can further comprise a step (d), of detecting a colorimetric and/or fluorescence output emitted from the nanoparticle bound to the bacterial cells. In some embodiments, the output is detectable by eye. In other embodiments, the output is detected via a detector.

In some embodiments, the colorimetric and/or fluorescence output emitted from the nanoparticle bound to the bacterial cells is measured or quantified by detecting a colorimetric and/or fluorescence output from the nanoparticles on the bacterial cells which are in turn attached to the porous substrate. The colorimetric output can be due to light absorption, light transmission, and/or reflection. Accordingly, the colorimetric and/or fluorescence output can be measured from the porous substrate. This provides a further advantage of ease of use for an on-site application as a solid (which is easily handled) is used.

In some embodiments, the method for quantifying bacterial cells in the sample can be completed in less than about 10 min. In this regard, the bacterial cells in the sample is quantifiable in less than about 10 min. In other embodiments, the amount of time required to quantify the bacterial cells is less than about 15 min, about 20 min, about 30 min, about 40 min, or 60 min.

In some embodiments, Gram-positive bacterial cells in the sample are quantifiable. In other embodiments, Gram-negative bacterial cells in the sample are quantifiable. In other embodiments, Gram-positive and Gram-negative bacterial cells in the sample are quantifiable. In other embodiments, Gram-positive or Gram-negative bacterial cells in the sample are quantifiable.

In some embodiments, when using a detector, the limit of detection for live bacterial cells in a sample is about $10^2$ cfu/mL. In other embodiments, when using a detector, the limit of detection for dead bacterial cells in a sample before step (c) is about $10^7$ cfu/mL. After washing, dead cells at $10^7$ cfu/ml no longer gives a staining signal.

In some embodiments, live bacterial cells in a sample is quantifiable from about $10^2$ cfu/mL to about $10^9$ cfu/mL. In some embodiments, dead bacterial cells in a sample is not quantifiable when less than about $10^7$ cfu/mL. In some embodiments, dead bacterial cells in a sample is quantifiable when more than about $10^7$ cfu/mL.

In some embodiments, when the sample comprises live bacterial cells and dead bacterial cells, the colorimetric and/or fluorescence output is emitted from the nanoparticle bound to only the live bacterial cells. In other embodiments, the live bacterial cells in the sample is at least about $10^2$ cfu/mL. In other embodiments, the dead bacterial cells in the sample is less than about $10^7$ cfu/mL.

In some embodiments, when the sample comprises Gram-positive bacterial cells and Gram-negative bacterial cells, the colorimetric and/or fluorescence output is emitted from the nanoparticle bound to both the Gram-positive bacterial cells and Gram-negative bacterial cells. Both the Gram-positive bacterial cells and Gram-negative bacterial cells are alive.

In some embodiments, the present invention discloses a variety of affinity-based nanostains (nanoparticles) for total bacteria count in a "filter & stain" method. These nanostains are nanomaterials conjugated with affinity-probes, recognizing cell wall molecular commonalities shared among bacteria. The nanomaterials either have intrinsic colour, such as metal nanoparticles, or emit fluorescence upon excitation, such as semiconductor nanorods. For total bacteria count, the affinity probes recognize the peptidoglycans (polymer of amino acids and saccharides) that form cell walls of Gram negative and Gram positive bacteria. The affinity probes can be lectins, BSA, aptamers, or antibodies. For demonstration, *Griphonia simplicifolia* II (GSII) lectin, BSA, and Antibac2 (AB2) aptamer were used. By using affinity probes, the main driving force for nanoparticle-bacterial binding will be the specific interaction between the affinity probes and the bacteria cells.

Based on the above, a general procedure to quantify Gram-positive and/or Gram-negative bacterial cells is as follows. A liquid sample containing bacterial cells is firstly prepared. For example, if a liquid food source is suspected of being contaminated with bacterial cells, an aliquot can be taken. If the food source is a solid, a swab can be taken and the adhered content on the swab dissociated using an appropriate solvent such as water or aqueous buffer solution. The porous substrate is positioned within a syringe cartridge and closed. The sample is then drawn up by a syringe, the syringe cartridge attached to the nozzle of the syringe and the sample is allowed to pass through the porous substrate under pressure. The aqueous nanoparticle solution is then passed through the porous substrate in a similar manner, followed by the second aqueous solution for washing. To determine if the sample contains bacterial cells, the porous substrate can be observed by eye. If bacterial cells are present, a colorimetric indication can be observed from the color of the nanoparticles (absorption, reflection or transmission) that are trapped or retained on the porous substrate. Fluorimetric indication can be observed under light excitation. Quantitative analysis can be obtained by using an appropriate detector.

Alternatively, and as another example, the liquid sample can be allowed to pass through the porous substrate using pumps. A similar procedure can be used with the aqueous nanoparticle solution and/or the second aqueous solution.

If the detected bacterial cells in the sample is observed to be outside the quantifiable range, the sample can be quantitatively diluted and re-analysed.

The present invention also discloses a device for quantifying bacterial cells in a sample in a liquid form, comprising:
    a) a porous substrate for trapping or retaining the bacterial cells on its surface thereof; and
    b) an aqueous nanoparticle solution comprising a plasmonic and/or fluorescent nanoparticle and a first ionic surfactant, the nanoparticle functionalised with an affinity probe for binding to said bacterial cells trapped or retained on the surface of the substrate via affinity binding; and
    c) a second aqueous solution for washing the unbound nanoparticle from the porous substrate;

wherein the bacterial cells in the sample is quantifiable by a colorimetric and/or fluorescence output emitted from the nanoparticle bound to the bacterial cells.

In some embodiments, the method of quantifying bacterial cells in a sample, comprises:
    a) passing the sample in a liquid form through a porous substrate, the porous substrate for trapping or retaining bacterial cells on its surface thereof;
    b) passing an aqueous nanoparticle solution through the porous substrate, the aqueous nanoparticle solution comprising a plasmonic and/or fluorescent nanoparticle and a first ionic surfactant, the nanoparticle functionalised with an affinity probe for binding to said bacterial cells trapped or retained on the surface of the substrate via affinity binding; and
    c) passing a second aqueous solution through the porous substrate, the second aqueous solution for washing the unbound nanoparticle from the porous substrate;
wherein the bacterial cells in the sample is quantifiable by a colorimetric and/or fluorescence output emitted from the nanoparticle bound to the bacterial cells;
wherein the porous substrate is a PVDF filter membrane;
wherein the plasmonic and/or fluorescent nanoparticle is a semiconductor nanorod; and
wherein the first ionic surfactant is CTAB.

In other embodiments, the device for quantifying bacterial cells in a sample comprises:
    a) a porous substrate for trapping or retaining the bacterial cells on its surface thereof; and
    b) an aqueous nanoparticle solution comprising a plasmonic and/or fluorescent nanoparticle and a first ionic surfactant, the nanoparticle functionalised with an affinity probe for binding to the bacterial cells via affinity binding; and
    c) a second aqueous solution for washing the unbound nanoparticle from the porous substrate;
wherein the bacterial cells in the sample is quantifiable by a colorimetric and/or fluorescence output emitted from the nanoparticle bound to the bacterial cells;
wherein the porous substrate is a PVDF filter membrane;
wherein the plasmonic and/or fluorescent nanoparticle is a semiconductor nanorod; and
wherein the first ionic surfactant is CTAB.

In some embodiments, the bacterial cells in the sample is quantifiable by measuring a colorimetric and/or fluorescence output emitted from the nanoparticles on the porous substrate. The colorimetric output can be due to light absorption, light transmission, and/or reflection.

In other embodiments, the device further comprises a detector. The detector is for quantifying the colorimetric and/or fluorescence output emitted from the nanoparticle bound to the bacterial cells. For example, the detector can be a UV-vis spectrometer, for detecting the colorimetric output. The detector can also be a fluorescence detector, for detecting the fluorescence output. The detector can further be a portable detector.

Advantageously, the device (comprising the consumables and detector) can be a handheld device, which allows for its ease of use for on-site application due to the simple filtering processes using syringe filters and small quantities of liquid reagent.

In some embodiments, the device is for quantifying Gram-positive and/or Gram-negative bacterial cells in the sample.

In some embodiments, when using the detector, the limit of detection for live bacterial cells in a sample is about $10^2$ cfu/mL. In some embodiments, live bacterial cells in a sample is quantifiable from about $10^2$ cfu/mL to about $10^9$ cfu/mL.

In some embodiments, when using the detector, the limit of detection for dead bacterial cells in a sample about $10^7$ cfu/mL. In some embodiments, dead bacterial cells in a sample is not quantifiable when less than about $10^7$ cfu/mL. In some embodiments, dead bacterial cells in a sample is quantifiable from about $10^7$ cfu/mL.

The present invention also discloses a kit for effecting the invention. The kit comprises an aqueous nanoparticle solution as disclosed herein and a second aqueous solution. The kit can be used for bacterial cell quantification. Advantageously, the second solution when used to wash the bacterial cell sample allows for the preferential quantification of live bacterial cells over dead bacterial cells by disturbing the affinity interaction of the nanoparticle with dead bacterial cells, which is not as strong as with live bacterial cells. This causes the nanoparticles to be washed off the dead bacterial cells, resulting in preferential quantification of live bacterial cells.

The present invention also discloses an aqueous nanoparticle solution, comprising a plasmonic and/or fluorescent nanoparticle and a first ionic surfactant. The nanoparticle is functionalised with an affinity probe. The affinity probe can be a protein, sugar binding protein, peptide or DNA aptamer.

In the kit, the aqueous nanoparticle solution may be provided as a neat or concentration solution. This is advantageous for transportation and storage. The user can then dilute the nanoparticle solution to a desired concentration for use. Accordingly, in an embodiment, the aqueous nanoparticle solution is at a concentration of about 2 nM to about 30 nM.

Similarly, the second aqueous solution can also be provided as a neat or concentrated solution. Accordingly, in an embodiment, the second surfactant in the second aqueous solution is at a concentration of about 0.5 wt/wt % to about 1 wt/wt %.

The kit can further comprise of the porous substrate.

Advantages of the present invention are as follows:

The affinity interactions between the affinity probes and common molecules on bacteria cell wall (such as peptidoglycans, etc) make the affinity-based nanostains specific to all bacteria cells.

This design principle is particularly suitable for F&B samples, considering that F&B may contain particulates or micelles with negative charge same as bacteria cells, where the earlier charge-based nanostain will lost the specificity.

Rapid (20 min—from sample handling to results)

The fluorescence-based nanostains allow bacteria detection in samples with background colour.

Semiconductor nanorod particle is brighter than its spherical quantum dot counterpart. The semiconductor nanorods require less amount of material (10 times lesser) than spherical quantum dots to get similar brightness on filter membrane.

Portable

Not sensitive to temperature changes/can be performed over a wide range of temperatures (5° C. to 80° C.).

Does not rely on enzymatic reaction

No/minimal sample treatment required

The present invention can be applied as an on-site total bacteria count from water, liquid F&B samples. The present invention can also be used for early detection of bacterial contamination in F&B and environment.

General Protocol

Figure 12:
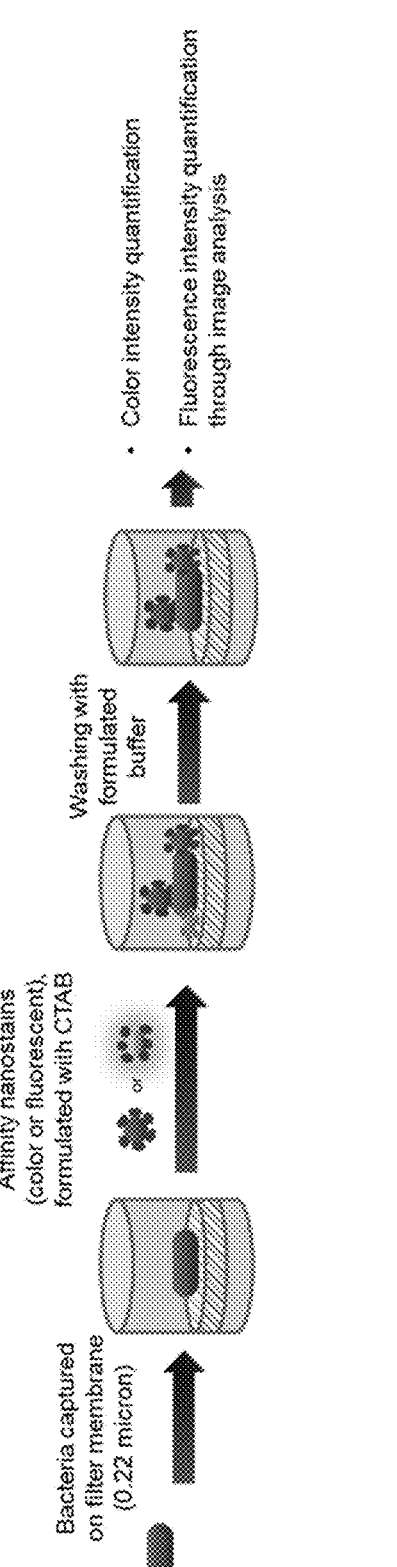
FIG. 12 illustrates an embodiment of the method of quantifying bacterial cells in a sample.

To use the affinity-based nanostains for total bacteria count in the "filter & stain" method (FIG. 12), typically 1 mL of bacteria samples were filtered using a size-exclusion syringe filter (0.22 μm pore size, 4 mm diameter). Optionally for sample with high non-bacteria particulates, before passing through the 0.22 μm filter, the sample can be first passed through a pre-filter (5 μm pore size filter, any diameter, material: Nylon, PVDF, or other hydrophilic membrane not adsorbing bacteria, however the membrane should not contain glass fibre) to remove larger particulates and prevent 0.22 μm filter jamming. Bacteria cell is smaller than 5 μm and can pass through the 5 μm pre-filter. The nanostains solution (200 μL) was then passed through the same filter to bind to the bacteria cells captured on the filter membrane. To prevent non-specific attachment of nanostains on the filter membrane, the nanostains solution is formulated with surfactant (such as CTAB) at optimized concentration. After 10 min incubation, 1 mL of washing solution was passed through to wash unbound nanostains from the filter. The washing solution can be water or water formulated with surfactant (Tween-20) for better differentiation of live and dead cells. After washing and drying with air, color stain or fluorescence stain from the nanostains on the filter membrane was quantified by using an in-house portable color reader or analyzed through image analysis under normal light (for color stain) or UV light (for fluorescence stain).

With the above nanomaterials and their formulations (staining solution and washing solution formulation), bacteria cells trapped on a filter membrane can be stained either giving a colour readout or a fluorescent readout. The assay process takes as short as 20 min (10 min incubation and 10 min filter handling).

The intensity of the colour or fluorescence is proportionally related to bacteria concentration. These affinity-based nanostains have been tested with Gram negative bacteria (such as *E. coli*) and Gram positive bacteria (such as *S. aureus*) in water.

The coloured metallic nanoparticle affinity-stain can detect bacteria from any solutions that do not significantly stain the filter membrane. The fluorescence-based nanostains allow bacteria detection in samples that stain the filters and can offer higher detection sensitivity than the colour-based nanostain using the same affinity probe.

Example I: Bacteria Detection Using Color Stain of GSII-AuNP

In this example, the affinity-based nanostain is developed from GSII lectin attached to gold nanoparticles (GSII-AuNPs). GSII lectin binds bacteria peptidoglycan especially on the N-acetylglucoseamine part of the peptidoglycans. The AuNPs are used as synthesized from $HAuCl_4$ reduction by sodium citrate. They are spherical in shape with diameter of around 13 nm. GSII lectin is attached to AuNPs through physical adsorption. The concentration of GSII is optimized at 0.1 mg/mL to prevent AuNPs aggregation in the presence of samples containing salt up to 30 g/L NaCl, which is high enough and close to seawater salinity (35 g/L) as the most hash real sample condition. For application in the "filter & stain" method, GSII-AuNPs solution is formulated with surfactant (such as CTAB) at optimized concentration of 5 mg/mL to prevent non-specific attachment of nanostains on the filter membrane.

The formulated GSII-AuNPs solution is used in "filter & stain" for total bacteria count using *E. coli* as a representative of Gram Negative bacteria and *S. aureus* as a representative of Gram Positive bacteria. Red color stain obtained from GSII-AuNPs bound to bacteria captured on the filter membrane is visible starting at of $10^6$ cfu/mL (FIG. 1).

Figure 2:
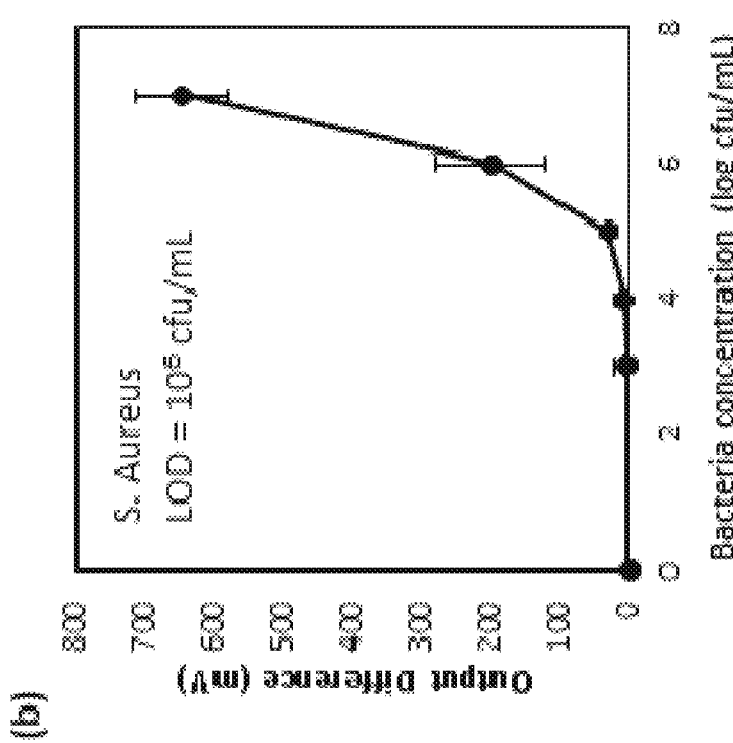
FIG. 2 illustrates output difference obtained from GSII-AuNPs staining on bacteria samples relative to blank (no bacteria) for (a) E. coli and (b) S. aureus in water, measured using a color detector.
Figure 2:
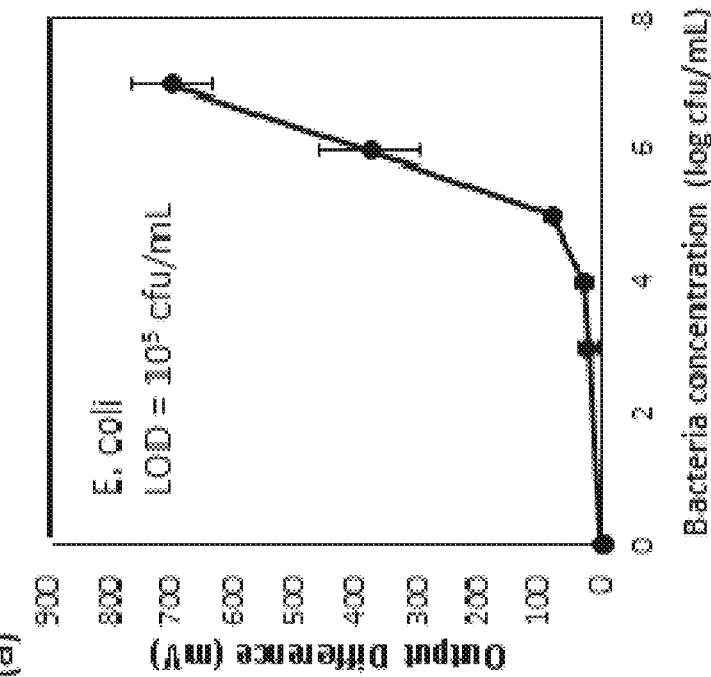

To obtain a quantitative colorimetric signal reading, an in-house customized portable colour detector was utilised to measure the reflected green light intensity from the filter membranes (this detector was used in the following color based examples as well). The difference of the detector output for *E. coli* and *S. aureus* samples relative to blank (no bacteria, i.e. 0 cfu/mL) are shown in FIGS. 2a and 2b, respectively.

Example II: Bacteria Detection Using Fluorescence Stain of GSII-QNRs

In this example, the affinity-based nanostain is developed from GSII lectin conjugated to CdSe/CdS core/shell nanorods (GSII-QNRs). The QNRs are 23 nm in length, 5 nm in width, exhibiting fluorescence emission peak at 590 nm. They are encapsulated with amphiphilic polymer with carboxylic acid functional groups. GSII lectin is conjugated to QNRs through covalent amine coupling using EDC/NHS chemistry.

For application in "filter & stain" method, GSII-QNRs concentration used to create significant fluorescence stain is 3.75 nM. This concentration is about 10 times lower than that is required for its spherical quantum dot counterpart. GSII-QNRs tend to stick on the filter membrane in the absence of bacteria. To prevent this nonspecific binding, the GSII-QNRs is formulated with a surfactant (such as CTAB) at optimized concentration of 4 mg/mL. The formulated GSII-QNRs solution is used in "filter & stain" for total bacteria count by using *E. coli* as a representative of Gram Negative bacteria and *S. aureus* as a representative of Gram Positive bacteria. Orange fluorescence stain from GSII-QNRs bound to bacteria captured on the filter membrane is visible in the concentration range of $10^4$-$10^7$ cfu/mL (FIG. 3). Stronger orange fluorescence emission can be seen for higher bacteria concentration.

To obtain a more quantitative fluorescence signal reading, image analysis by ImageJ software that measures the light intensity from selected membrane area was utilised. The increase in fluorescence stain intensity for a bacteria sample is calculated as percentage of intensity increment ($\% I_{in}$) relative to the fluorescence intensity of a blank sample:

$$\% \, I_{in} = \frac{I_s - I_b}{I_b} \times 100\%$$

Where $I_s$ is the intensity value of the sample, and $I_b$ is the intensity value of the blank (no bacteria).

For *E. coli*, slight intensity increase can be observed at $10^3$ cfu/mL. For *S. aureus*, clear intensity increment can be observed starting at $10^3$ cfu/mL. This LOD at $10^3$ cfu/mL is lower than the LOD observed by using the same lectin in color based assay by using GSII-AuNPs ($10^5$ cfu/mL).

Figure 5:
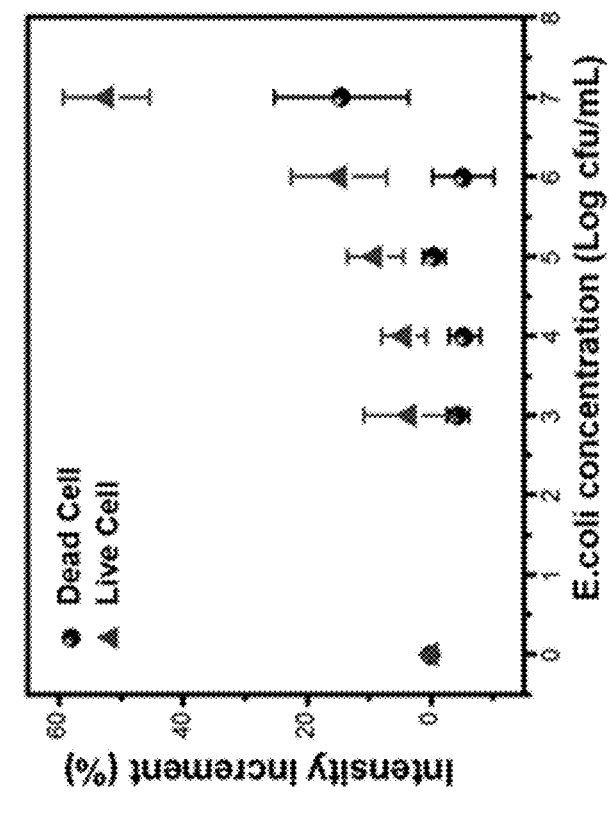
FIG. 5 illustrates (a) visual outcome of GSII-QNRs staining in "filter & stain" method for dead E. coli cells ($10^3$-$10^7$ cfu/mL equivalent), as taken by using a mobile phone camera under UV light (365 nm), (b) percentage of intensity increment (average and standard deviation) for live and dead E. coli cells based on image analysis.
Figure 5:

To study whether the GSII-QNRs respond to dead bacteria cells, we prepared dead *E. coli* cells by autoclaving live *E. coli* cells of a known concentration, and tested them using the "filter & stain" method. FIG. 5a shows the images of GSII-NRs stain for dead *E. coli* cells ($10^3$-$10^7$ cfu/mL equivalent) as taken by a cell-phone camera. We found that fluorescence can be seen from dead *E. coli* cells prepared from $10^7$ cfu/mL live cells. Below this concentration, the stain is not observable. On the other hand, for live cells, the stain can be observed at much lower concentration as demonstrated in the previous section. FIG. 5b shows the intensity increment comparison of GSII-QNRs stain for live and dead bacteria in a range of bacteria concentrations.

To increase the contrast of stain intensity between live and dead cells, the nanostain washing solution is formulated by adding Tween-20 surfactant into water (0.5%). FIG. 6a shows the comparison of the visual outcome with and without adding Tween 20 in the washing step for live and dead *E. coli* cells at $10^7$ cfu/mL equivalent. Based on the image analysis, adding Tween-20 in the washing buffer (blue bar) results in an intensity increment ratio of 5.8 between live to dead cell. This ratio is larger than that (only 3.5) without using Tween 20 (pink bar). These results suggest that adding Tween-20 increase the intensity differentiation between live and dead cells in the GSII-QNRs based "filter & stain" assay. The largely reduced stain for dead cells in the presence of Tween 20 could be because Tween-20 as a surfactant washes away weakly bound GSII-QNRs on dead bacteria cells with denatured peptidoglycan.

Figure 7:
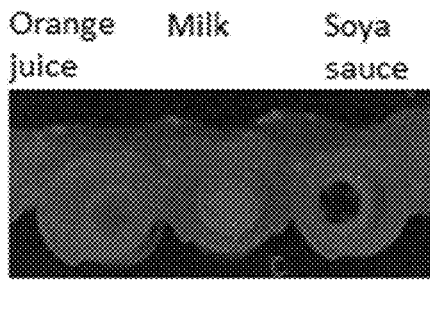
FIG. 7 illustrates (a) no fluorescence background for F&B samples (orange juice, milk, and soya sauce) on the membrane under UV light excitation, (b) GSII-QNRs staining for E. coli cells ($10^7$ cfu/mL) spiked in sterile orange juice and soya sauce; the F&B samples were diluted 50 times in water to prevent filter membrane jamming; images are taken by using a mobile phone camera under UV light (365 nm)
Figure 7:
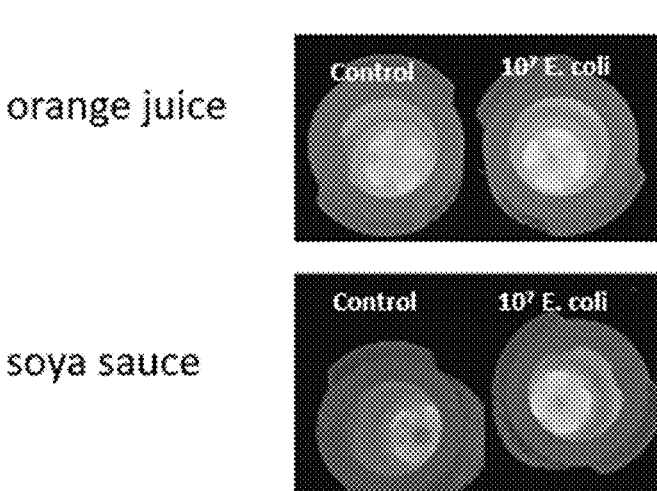

The feasibility of using fluorescence stain of GSII-QNRs for bacteria detection in F&B samples was also tested. Most F&B samples would have background color that may interfere with the color based metallic nanostains, but F&B samples usually do not have significant fluorescence background (FIG. 7a). Preliminary test shows that fluorescence stain from GSII-QNRs can detect *E. coli* spiked in orange juice and soya sauce as shown in FIG. 7b.

Example III: Bacteria Detection Using Color Stain of BSA-AuNPs

In this example, BSA protein is used as an affinity probe. BSA has affinity to bacteria peptidoglycan, lipopolysaccharides and lipoteichoic acid of bacteria. BSA is attached to AuNPs through physical adsorption. The obtained BSA-AuNPs solution is formulated with surfactant (CTAB 6 mg/mL) to maintain significant color signal for bacteria detection and prevent non-specific attachment of nanostains on the filter membrane.

Figure 8:
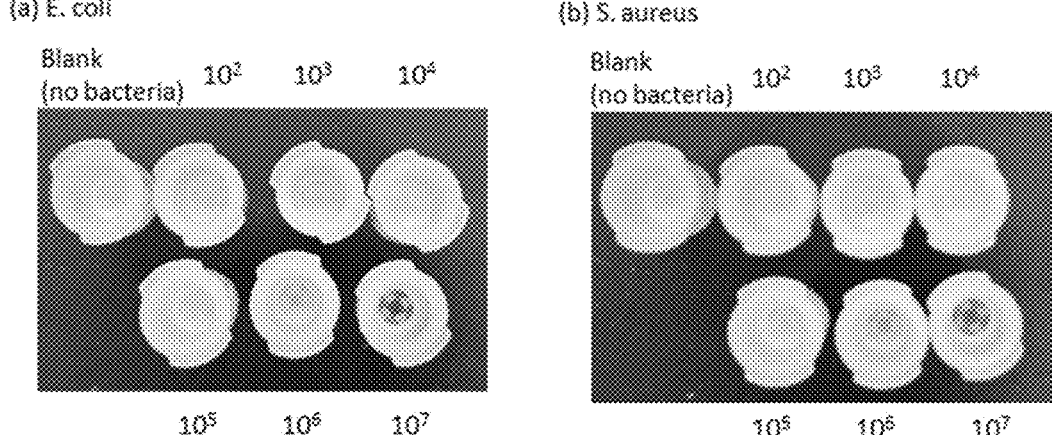
FIG. 8 illustrates results of BSA-AuNPs staining in "filter & stain" method for (a) E. coli and (b) S. aureus in water ($10^2$-$10^7$ cfu/mL); images were taken by using a mobile phone camera.

The formulated BSA-AuNPs solution is used in "filter & stain" for total bacteria count, with *E. coli* as a representative of Gram Negative bacteria and *S. aureus* as a representative of Gram Positive bacteria in water. Red color stain obtained from BSA-AuNPs bound to bacteria is visible starting at bacteria concentration of $10^6$ cfu/mL visually (FIG. 8).

Figure 9:
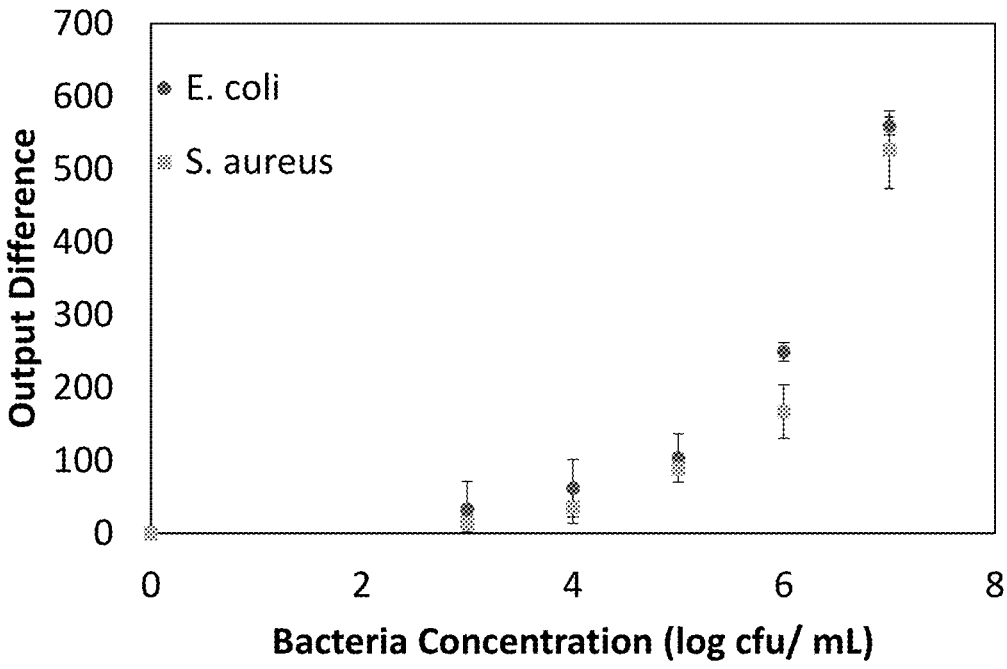
FIG. 9 illustrates result of BSA-AuNPs staining in "filter & stain" method; the output difference for *E. coli* and *S. aureus* relative to blank (no bacteria) sample in water was measured using a color detector.

To obtain a quantitative colorimetric signal reading, an in-house customized portable colour detector was used to measure the reflected green light intensity from the filter membranes. The difference of the detector output for bacteria samples relative to blank (no bacteria) for *E. coli* and *S. aureus* at various concentrations are shown in FIG. 9. Clear increase in output difference can be observed for *E. coli* and *S. aureus* at concentration of $10^5$ cfu/mL.

Example IV: Bacteria Detection Using Color Stain of AB2 Aptamer-AuNPs

In this example the affinity probe used is Antibac 2 (AB2) aptamer that recognizes bacteria peptidoglycan. This AB2 aptamer has a sequence of TCG CGC GAG TCG TCT AGG GGA CTA GAG GAC TTG TGC GGC CCC GCA TCG TCC TCC C (55 mer). It is conjugated to gold nanoparticles (AuNPs) through thiol-gold covalent interaction. Particularly, the AB2 is modified with thiol group on its 5' end, with a 15 carbon spacer between the thiol group and the functional sequence, to maintain aptamer conformation from spreading on AuNPs surface. The starting concentration of AB2 to be conjugated on AuNPs is optimized at 320 nM. The obtained AB2-AuNPs solution is formulated with surfactant (CTAB 6 mg/mL) to maintain significant color signal for bacteria detection and prevent non-specific attachment of nanostains on the filter membrane.

Figure 10:
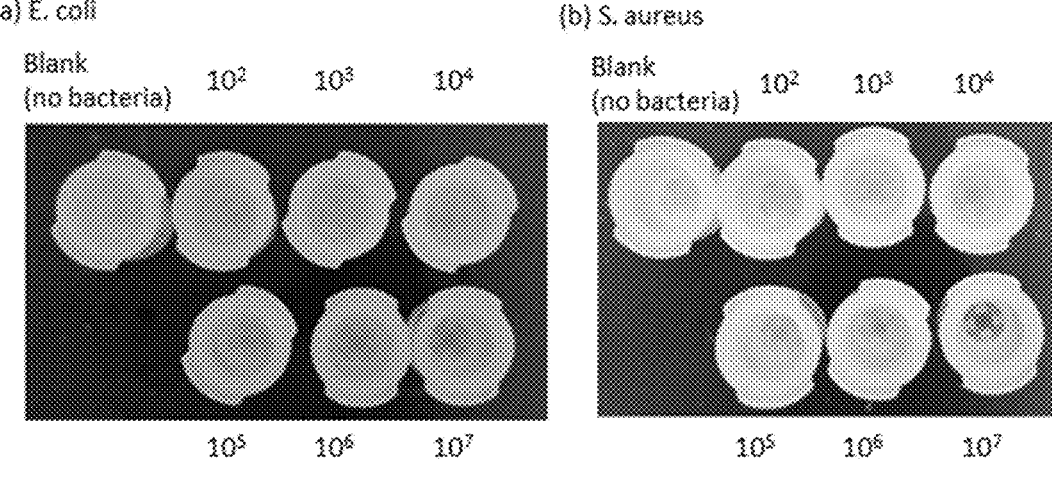
FIG. 10 illustrates visual outcome of AB2-AuNPs staining in "filter & stain" method for (a) *E. coli* and (b) *S. aureus* in water with concentration range of $10^2$-$10^7$ cfu/mL; images were taken by using a mobile phone camera.

The formulated AB2-AuNPs solution is used in "filter & stain" for total bacteria count, with *E. coli* as a representative of Gram Negative bacteria and *S. aureus* as a representative of Gram Positive bacteria in water. Red color stain obtained from AB2-AuNPs bound to bacteria ($10^2$-$10^7$ cfu/mL) captured on the filter membrane can be seen visually (FIG. 10).

Figure 11:
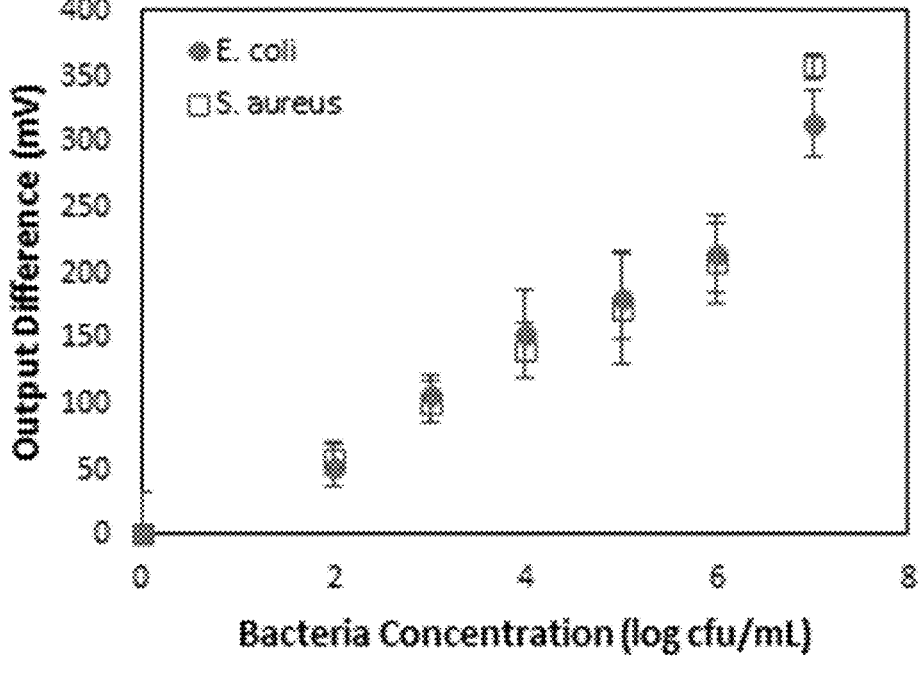
FIG. 11 illustrates output difference relative to blank sample for *E. coli* and *S. aureus* in water with concentration range of $10^2$-$10^7$ cfu/mL, measured using a color detector.

To obtain a quantitative colorimetric signal reading, an in-house customized portable color detector was used to measure the reflected green light intensity from the filter membranes. The difference of the detector output for bacteria samples relative to blank (no bacteria, i.e. 0 cfu/mL) are shown in FIG. 11. Increase in output difference can be observed for *E. coli* and *S. aureus* at concentration as low as $10^2$ cfu/mL, and the increase in output difference correlates well to the increase of bacteria concentration.

It will be appreciated that many further modifications and permutations of various aspects of the described embodiments are possible. Accordingly, the described aspects are intended to embrace all such alterations, modifications, and variations that fall within the spirit and scope of the appended claims.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A method of quantifying bacterial cells in a sample, comprising:

a) passing the sample in a liquid form through a porous substrate, the porous substrate for trapping or retaining bacterial cells on its surface thereof;

b) passing an aqueous nanoparticle solution through the porous substrate, the aqueous nanoparticle solution comprising a plasmonic and/or fluorescent nanoparticle and a first ionic surfactant, the nanoparticle functionalised with an affinity probe for binding to said bacterial cells trapped or retained on the surface of the substrate via affinity binding; and c) passing a second aqueous solution through the porous substrate, the second aqueous solution for washing the unbound nanoparticle from the porous substrate; wherein the bacterial cells in the sample are quantifiable by a colorimetric and/or fluorescence output emitted from the nanoparticle bound to the bacterial cells.

2. The method according to claim 1, wherein the first ionic surfactant is selected from cetrimonium bromide (CTAB), cetrimonium chloride (CTAC) or sodium dodecyl sulfate (SDS), and/or wherein the first ionic surfactant in the first solution is at a concentration of at least 2 mg/mL.

3. The method according to claim 1, wherein the plasmonic and/or fluorescent nanoparticle is selected from metallic nanoparticles, II-VI binary, ternary and quaternary semiconductor nanocrystals, IV-VI semiconductor nanocrystals, III-V semiconductor nanocrystals, I-V semiconductor nanocrystals, I-III-V semiconductor nanocrystals, group IV elemental semiconductor nanocrystals, $Cu^+$ and $Mn^{2+}$ doped semiconductor nanocrystals, and their related core/shell structures thereof, or wherein the plasmonic and/or fluorescent nanoparticle is selected from gold nanoparticles, silver nanoparticles or CdSe/CdS core/shell nanorods.

4. The method according to claim 1, wherein the nanoparticle is functionalised with an affinity probe selected from protein, sugar binding protein, peptide or aptamer, such as *Griffonia simplicifolia* II (GSII) lectin, BSA, and Antibac2 (AB2) aptamer, and/or wherein a ratio of affinity probe to nanoparticle is about 1:1 to about 100:1.

5. The method according to claim 1, wherein the nanoparticle is at a concentration of about 2 nM to about 30 nM.

6. The method according to claim 1, wherein step (b) further comprises incubating the porous substrate with the first solution for at least 10 min.

7. The method according to claim 1, wherein the nanoparticle is attachable to the bacterial cells via non-covalent interaction, wherein the non-covalent interaction is selected from electrostatic interaction, ionic bonding, Hydrogen bonding, Van der Waals interaction or a combination thereof.

8. The method according to claim 1, wherein the second aqueous solution is a protein dissociation buffer such as glycine-HCl buffer at about pH 2.8 to about pH 3.5 or citric acid buffer at about pH 3.

9. The method according to claim 1, wherein the second aqueous solution comprises a second surfactant selected from Tween-20, CTAB, CTAC, SDS, and/or wherein the second surfactant in the second aqueous solution is at a concentration of about 0.5 wt/wt % to about 1 wt/wt %.

10. The method according to claim 1, wherein step (c) further comprises incubating the porous substrate with the second aqueous solution for at least 10 min.

11. The method according to claim 1, wherein the colorimetric and/or fluorescence output emitted from the nanoparticle bound to the bacterial cells is measured or quantified by detecting a colorimetric and/or fluorescence output from the nanoparticles on the porous substrate.

12. The method according to claim 1, wherein the colorimetric and/or fluorescence output emitted from the nanoparticle bound to the bacterial cells is detectable by eye.

13. The method according to claim 1, further comprising a step of quantifying the colorimetric and/or fluorescence output emitted from the nanoparticle bound to the bacterial cells via a detector.

14. The method according to claim 1, for quantifying Gram-positive and/or Gram-negative bacterial cells in the sample.

15. The method according to claim 1, wherein live bacterial cells in a sample are quantifiable from about $10^2$ cfu/mL to about $10^9$ cfu/mL, and/or wherein dead bacterial cells in a sample are quantifiable from more than about $10^7$ cfu/mL.

16. A device for quantifying bacterial cells in a sample in a liquid form, comprising:

a) a porous substrate for trapping or retaining the bacterial cells on its surface thereof; and b) an aqueous nanoparticle solution comprising a plasmonic and/or fluorescent nanoparticle and a first ionic surfactant, the nanoparticle functionalised with an affinity probe for binding to said bacterial cells trapped or retained on the surface of the substrate via affinity binding; and c) a second aqueous solution for washing the unbound nanoparticle from the porous substrate;

wherein the bacterial cells in the sample are quantifiable by a colorimetric and/or fluorescence output emitted from the nanoparticle bound to the bacterial cells.

17. The device according to claim 16, wherein the porous substrate has a pore size of about 0.22 μm.

18. The device according to claim 16, further comprising a detector for quantifying the colorimetric and/or fluorescence output emitted from the nanoparticle bound to the bacterial cells.

19. The device according to claim 16, for quantifying Gram-positive and/or Gram-negative bacterial cells in the sample.

20. The device according to claim 16, wherein the limit of detection for live bacterial cells in a sample is about $10^2$ cfu/mL, and/or wherein the limit of detection for dead bacterial cells in a sample is about $10^7$ cfu/mL.

$$* \quad * \quad * \quad * \quad *$$